(12) United States Patent
Yamamoto

(10) Patent No.: US 8,257,535 B2
(45) Date of Patent: Sep. 4, 2012

(54) MANUFACTURING METHOD OF ABSORBENT ARTICLE

(75) Inventor: Hiroki Yamamoto, Kanonji (JP)

(73) Assignee: Uni-Charm Corporation, Ehime (JP)

( * ) Notice: Subject to any disclaimer, the term of this patent is extended or adjusted under 35 U.S.C. 154(b) by 439 days.

(21) Appl. No.: 12/389,961

(22) Filed: Feb. 20, 2009

(65) Prior Publication Data

US 2010/0050411 A1 Mar. 4, 2010

(30) Foreign Application Priority Data

Aug. 29, 2008 (JP) ................................ P2008-222490

(51) Int. Cl.
*A61F 13/15* (2006.01)
(52) U.S. Cl. ........................ 156/204; 156/226; 156/269
(58) Field of Classification Search ........................ None
See application file for complete search history.

(56) References Cited

U.S. PATENT DOCUMENTS

| | | | | |
|---|---|---|---|---|
| 3,773,002 A | * | 11/1973 | Burton | 112/470.05 |
| 3,850,085 A | * | 11/1974 | Klemm | 493/131 |
| 4,410,390 A | * | 10/1983 | Farrell | 156/461 |
| 5,575,781 A | * | 11/1996 | DeBusk | 604/362 |
| 5,902,222 A | * | 5/1999 | Wessman | 493/439 |
| 6,913,664 B2 | * | 7/2005 | Umebayashi et al. | 156/64 |
| 2003/0084984 A1 | * | 5/2003 | Glaug et al. | 156/204 |
| 2006/0151091 A1 | * | 7/2006 | Komatsu | 156/161 |

FOREIGN PATENT DOCUMENTS

JP 2005-046246 A 2/2005

* cited by examiner

*Primary Examiner* — John L. Goff
*Assistant Examiner* — Barbara J. Musser
(74) *Attorney, Agent, or Firm* — Lowe, Hauptman, Ham & Berner, LLP

(57) ABSTRACT

A manufacturing method of an absorbent article according to the present invention includes the steps of a leg circumference forming process of forming a leg circumferential region on a web which is continuously fed in an MD, in a conveyance device, and a folding process of folding the web in two after the leg circumference forming process, so that a second half region on one divided by a center line in a CD comes closer to or overlaps a first half region on the other side. In the folding process, the first half region is conveyed on a conveyance belt which drives horizontally in parallel to an installation surface of the conveyance device (for example, a folding device) and the second half region is folded towards the first half region by a guide unit that guides the second half region.

10 Claims, 5 Drawing Sheets

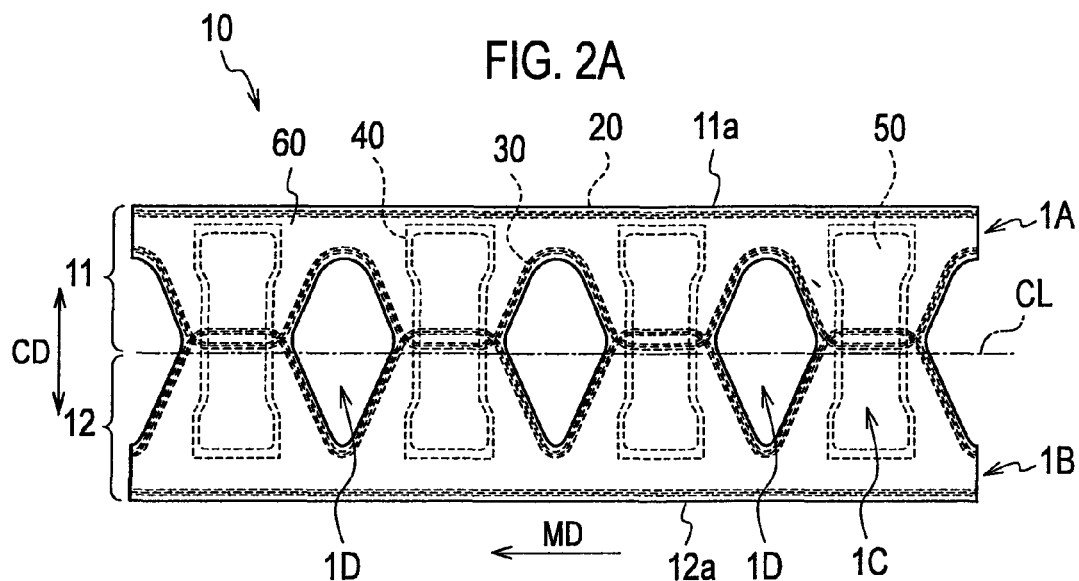
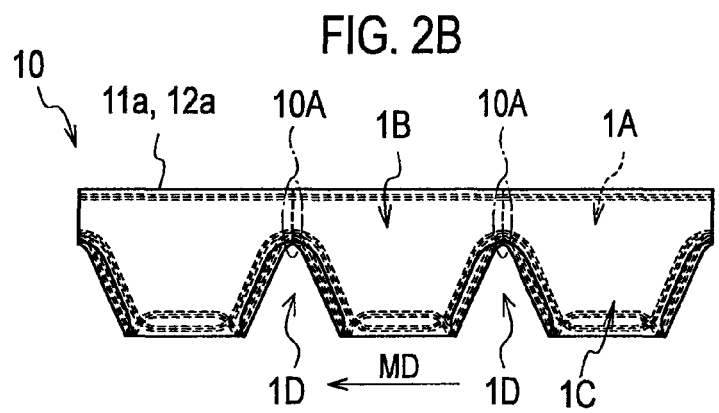
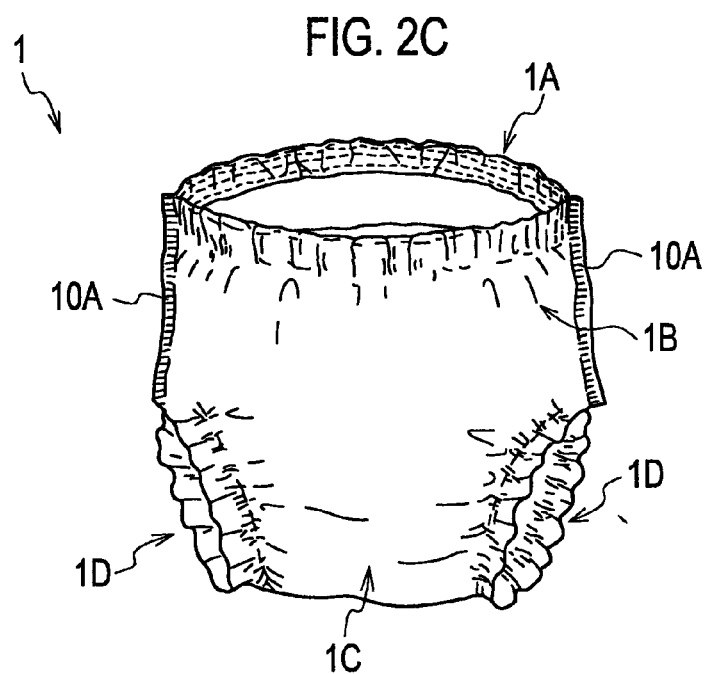

MANUFACTURING METHOD OF ABSORBENT ARTICLE

BACKGROUND OF THE INVENTION

1. Field of the Invention

The present invention relates to a manufacturing method of an absorbent article, in which a web is folded in two in a direction perpendicular to a conveyance direction of the web.

2. Description of the Related Art

Conventionally, in a manufacturing method of an absorbent article such as a disposable diaper, leg circumferential regions (for example, leg holes) are formed on a web on which individual members (for example, a gather, a waterproof sheet, an absorber, and a top sheet) are laminated. The web on which the leg circumferential regions are formed is folded in two at the center line in a direction (Crossing Direction (CD)) perpendicular to a conveyance direction (Machine Direction (MD)) of the web.

For example, in the folding process of folding the web in two, a first half region on one side divided by the center line in the CD is conveyed between multiple rollers which are arranged at predetermined spacing in the conveyance direction of the web. At this time, a second half region on the other side of the center line in the CD is folded by guide means towards the first half region using a folding center bar as a reference (for example, see Japanese Patent Application Publication No. 2005-46246 (pages 6 and 7, FIGS. 3 and 4)).

However, the above-described manufacturing method of an absorbent article has the following problem. That is, the first half region is conveyed with being partially supported by the multiple rollers which are arranged at predetermined spacing. Therefore, the first half region is suspended in the air at portions between the multiple rollers.

At this time, the crotch region of the web on which a waterproof sheet and an absorber are laminated comes into contact with the guide means or the folding center bar, and therefore conveyance of a crotch region gets behind conveyance of a waistline region. Accordingly, the second half region is sometimes folded towards the first half region with the crotch region being twisted. This damages the appearance of the absorbent article or generates a manufacturing failure of the absorbent article in processes after the folding process.

Furthermore, if the second half region is folded towards the first half region with the crotch region being twisted, the twist affects a portion including the waistline regions and the crotch region in both of the first half region and the second half region. Accordingly, a distortion and a deformation entirely spread over the absorbent article. In particular, the twist affects greatly in the absorbent article having a stretching property. Thus, there is a room for improvements.

Thus, the present invention has been made in light of the foregoing situation. Accordingly, an object of the present invention is to provide a manufacturing method of an absorbent article, which is capable of preventing a manufacturing failure of an absorbent article.

SUMMARY OF THE INVENTION

To solve the above-described problem, the present invention has the following aspects. Firstly, a first aspect of the present invention provides that in a conveyance device (for example, first to fourth conveyance rollers R1 to R4), included are a leg circumference forming process of forming a leg circumferential region (leg circumferential region 1D) on a web (web 10) which is continuously fed in a conveyance direction (MD), and a folding process of folding the web in two after the leg circumference forming process, so that a second web half region (second half region 12) on one side divided by a center line (center line CL) in a direction (CD) perpendicular to a conveyance direction of the web comes closer to or overlaps a first half region (first half region 11) on the other side, wherein in the folding process, the first half region is conveyed on a conveyance belt (conveyance belt 122) and the second half region is folded towards the first half region by a guide unit (guide means 140) that guides the second half region.

The present invention can provide a manufacturing method of an absorbent article, which can prevent a manufacturing failure of an absorbent article.

BRIEF DESCRIPTION OF THE DRAWINGS

FIG. 2 is a view showing a web 10 (absorbent article 1) according to the present embodiment.

DESCRIPTION OF THE PREFERRED EMBODIMENT

Figure 1:
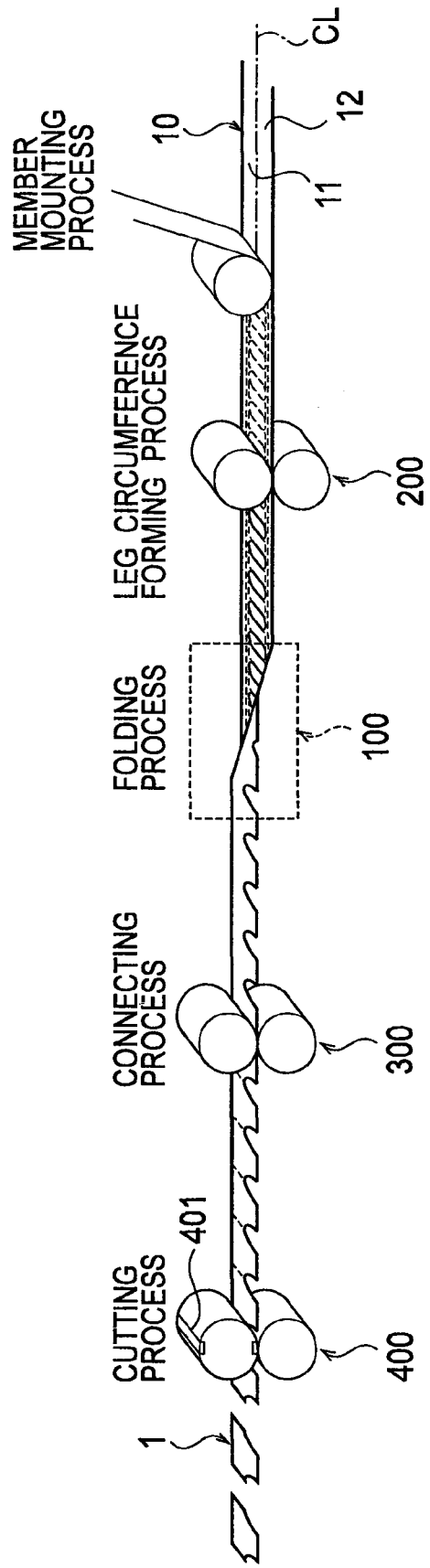
FIG. 1 is a schematic view showing a manufacturing method of an absorbent article 1 according to the present embodiment.

An embodiment of the present invention will be described below by referring to the drawings. Specifically, the description will be given of: (1) Manufacturing Method of Absorbent Article; (2) Configuration of Folding Device; and (3) Other Embodiments.

In the following description of the drawings, same or similar reference symbols are given to denote same or similar portions. However, it should be noted that the drawings are schematic and ratios of dimensions and the like are different from actual ones.

Therefore, specific dimensions and the like should be determined by taking into consideration the following description. Moreover, as a matter of course, also among the drawings, there are included portions in which dimensional relationships and ratios are different from each other.

(1) Manufacturing Method of Absorbent Article

Firstly, the manufacturing method of an absorbent article 1 according to the present embodiment will be described by referring to FIGS. 1 and 2. FIG. 1 is a schematic view showing the manufacturing method of an absorbent article 1 according to the present embodiment. FIG. 2 is a view showing a web 10 (the absorbent article 1) according to the present embodiment. Note that the absorbent article 1 according to the present embodiment is a disposable diaper with waistline members.

As shown in FIG. 1, the manufacturing method of the absorbent article 1 includes at least a member mounting process, a leg circumference forming process, a folding process, a connecting process, and a cutting process.

(1-1) Member Mounting Process

In the member mounting process, individual members are mounted on the web 10 (for example, a continuum of an outer sheet). The individual members include, for example, as shown in FIG. 2(a), gathers (a fit gather 20 and a leg gather 30), a waterproof sheet 40, an absorber 50, and a top sheet 60.

Here, as shown in FIG. 2(a) to FIG. 2(c), the web 10 includes waistline regions 1A and 1B corresponding to waistline members (waistline portions) of the absorbent article 1, a crotch region 1C positioned between the waistline regions 1A and 1B, and leg circumferential regions 1D positioned on both sides of the crotch region 1C.

The waistline regions 1A and 1B have a stretching property in a conveyance direction (MD) of the web 10. For example, the waistline regions 1A and 1B may have a stretching property in the MD by being provided with the fit gather 20 or may have a stretching property in the MD by forming the web 10 itself using a sheet having a stretching property.

The crotch region 1C has a stretching property in a direction (CD) perpendicular to the MD. For example, the crotch region 1C may have a stretching property in the CD by being provided with the leg gather 30 or may have a stretching property in the CD by forming the web 10 itself using a sheet having a stretching property.

(1-2) Leg Circumference Forming Process

In the leg circumference forming process, leg circumferential regions 1D (for example, leg holes) are formed in the web 10 on which the individual members are mounted by cut rollers 200.

(1-3) Folding Process

In the folding process, the web 10 on which the leg circumferential regions 1D are formed is folded in two by a folding device (see, FIGS. 3 and 4) to be described later at the center line CL in the CD of the web 10. That is, the web is folded in two in such a way that a second half region 12 on one side divided by the center line CL would come closer to or overlap a first half region 11 on the other side thereof. With this, a side edge portion 12a of the second half region 12 matches a side edge portion 11a of the first half region 11 (see, FIG. 2(b)).

(1-4) Connecting Process

In the connecting process, boundary regions 10A (see, FIG. 2(b)) of individual absorbent articles 1 on the web 10 folded in two are connected by a connecting device 300. For example, the boundary regions 10A are connected by a supersonic method, a heat embossing method, or the like. Note that a folding center bar 130 to be described later is used between the folding process and the connecting process.

(1-5) Cutting Process

In the cutting process, using a cutting device 400 with a cutting blade 401, one portion of the boundary regions 10A on the web 10 is cut in the CD to form an absorbent article 1 (see, FIG. 2(c)).

Here, the web 10 which is conveyed after the folding process is conveyed with being sandwiched by one pair of a first sandwich belt 501 and a second sandwich belt 502 (see, FIGS. 3 and 4) to be described later. For example, the web 10 is conveyed with being sandwiched by the first sandwich belt 501 and the second sandwich belt 502 between the folding process and the connecting process and between the connecting process and the cutting process.

(2) Configuration of Folding Device

Figure 3:
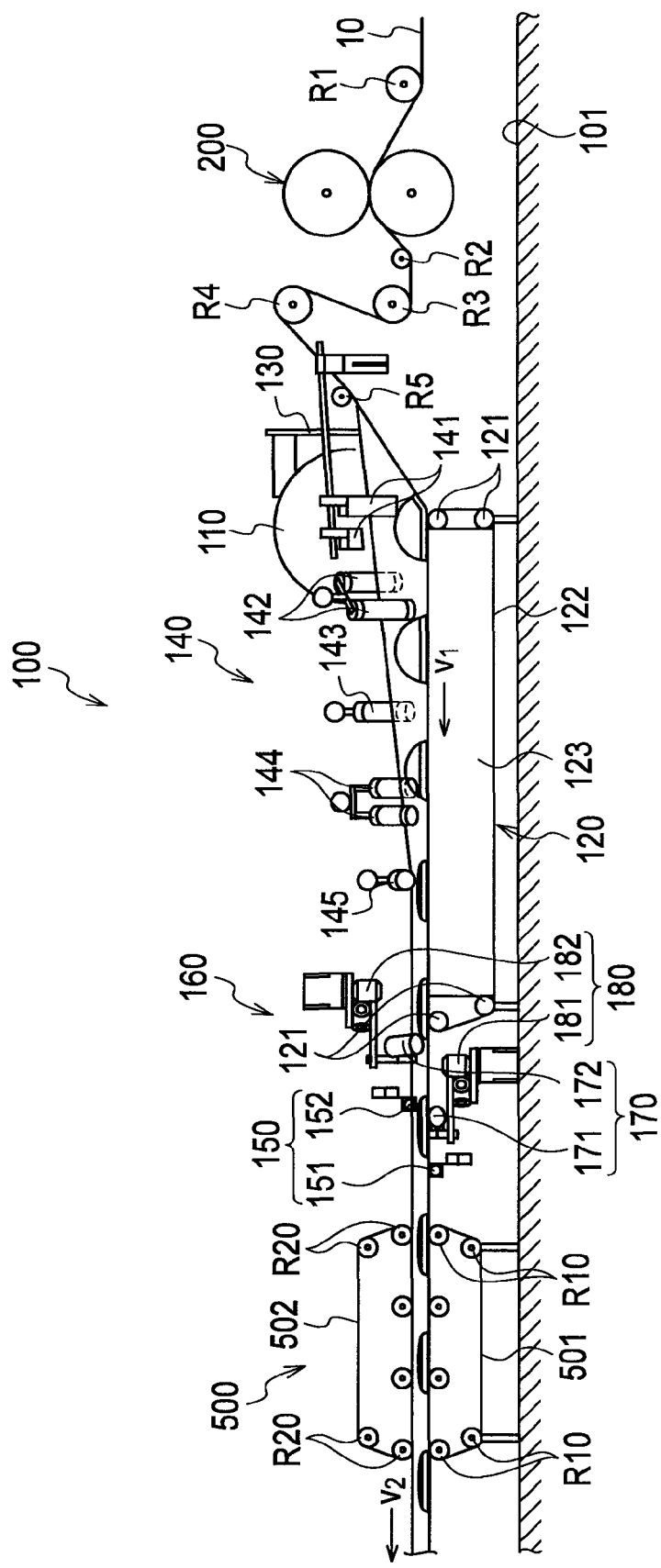
FIG. 3 is a side view showing a folding device 100 according to the present embodiment.
Figure 4:
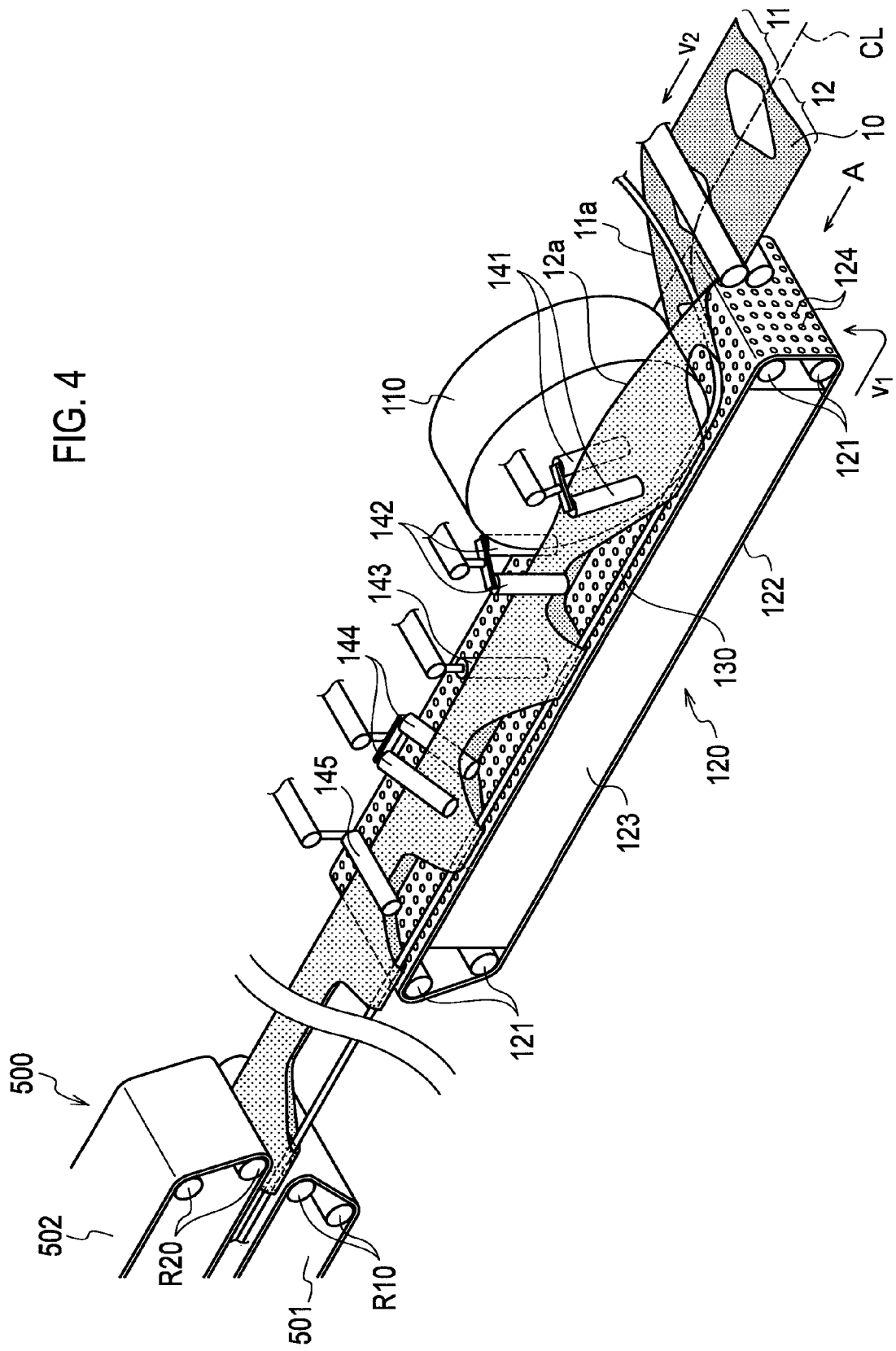
FIG. 4 is a perspective view showing the folding device 100 according to the present embodiment.
Figure 5:
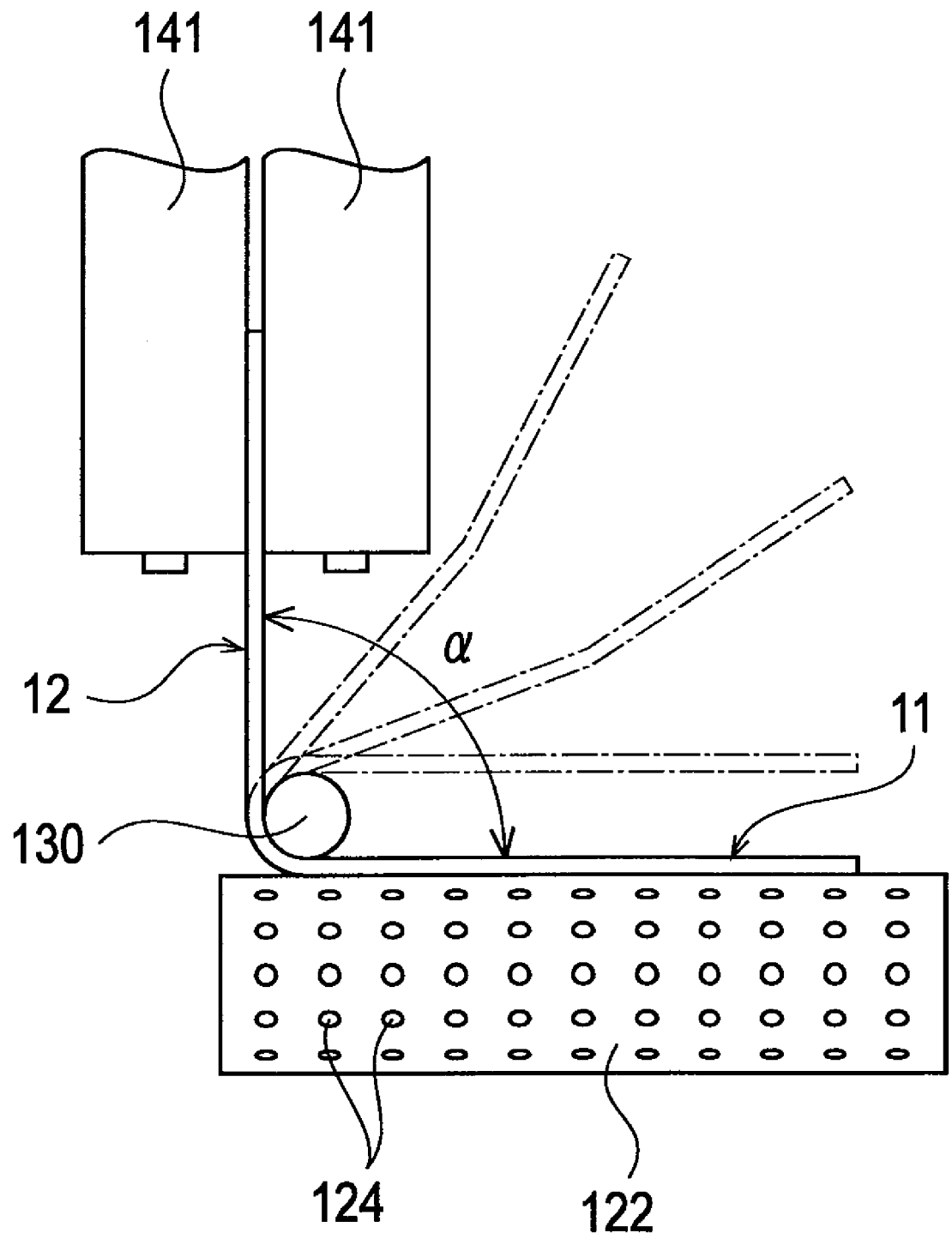
FIG. 5 is a view seen from the direction of an arrow (a view seen from the direction of the arrow A in FIG. 4) showing the folding device 100 according to the present embodiment.

Next, the configuration of the folding device 100 according to the present embodiment will be described by referring to FIGS. 3 to 5. FIG. 3 is a side view showing the folding device 100 according to the present embodiment. FIG. 4 is a perspective view showing the folding device 100 according to the present embodiment. FIG. 5 is a view seen from the direction of an arrow (a view seen from the direction of the arrow A in FIG. 4) showing the folding device 100 according to the present embodiment.

As shown in FIGS. 3 and 4, the folding device 100 is provided between a pair of the cut rollers 200 forming the above-described leg circumferential regions 1D and the sandwich belt conveyor 500 sandwiching the web 10 conveyed after the folding process.

Note that the web 10 is fed to the pair of the cut rollers 200 through a first conveyance roller R1. The web 10 is fed to the folding device 100 through a second conveyance roller R2, a third conveyance roller R3, a fourth conveyance roller R4, and a fifth conveyance roller R5. Note that the first to fourth conveyance rollers R1 to R4 respectively rotate around shafts thereof.

The folding device 100 includes a large diameter roller 110, a conveyance belt conveyor 120, a folding center bar 130, guide means 140, position detecting means 150, and position control means 160.

The large diameter roller 110 is provided between the fifth conveyance roller R5 and the guide means 140. The large diameter roller 110 conveys the first half region 11 of the web 10 between the large diameter roller 110 and a conveyance belt 122 to be described later. The large diameter roller 110 maintains the first half region 11 in a substantially horizontal state. The large diameter roller 110 has a width exceeding half the width of the web 10 which is folded in two. Note that the large diameter roller 110 rotates around a shaft thereof.

The conveyance belt conveyor 120 is provided between the large diameter roller 110 and the sandwich belt conveyor 500. The conveyance belt conveyor 120 conveys the first half region 11 in a substantially horizontal state in relation to a supporting surface 101 of the folding device 100.

The conveyance belt conveyor 120 is formed of the conveyance belt 122 winding around the multiple rollers 121, driving means (unillustrated) causing the conveyance belt 122 to wind around the multiple rollers 121, and suction means 123 sucking in outer air.

The conveyance belt 122 drives in a substantially horizontal state in relation to the supporting surface 101 of the folding device 100. It is preferable that a driving speed $v_1$ of the conveyance belt 122 be the same as a conveyance speed $v_2$ of the web 10. In the conveyance belt 122, multiple suction holes 124 sucking in the first half region 11 (see, FIGS. 4 and 5) are formed. That is, with the suction of the suction means 123 through the suction holes 124, the first half region 11 is conveyed on the conveyance belt 122 while being sucked.

The folding center bar 130 is provided in at least a position between a vicinity of the fifth conveyance roller R5 and the above-described connecting device 300 (see, FIG. 1) by way of a side of the sandwich belt conveyor 500. The folding center bar 130 divides the first half region 11 and the second half region 12 between the first half region 11 and the second half region 12 (that is, in the center line CL in the CD of the web 10).

The folding center bar 130 extends in the MD and is provided substantially parallel to the conveyance belt 122. Also, the folding center bar 130 is positioned on the conveyance belt 122 (see, FIG. 4).

The guide means 140 is provided between the fifth conveyance roller R5 and the sandwich belt conveyor 500. The guide means 140 guides the second half region 12 in a way that the side edge portion 12a of the second half region 12 is flush with the side edge portion 11a of the first half region 11.

The guide means 140 is formed of one pair of first guide rollers 141, one pair of second guide rollers 142, a third guide roller 143, one pair of fourth guide rollers 144, and a fifth guide roller 145.

The first guide rollers 141 raise the second half region 12 through the folding center bar 130. As shown in FIG. 5, from the first guide rollers 141 to the fifth guide roller 145, an inclination angle α of the second half region 12 in relation to the first half region 11 (a folding angle of the crotch region 1C) becomes gradually smaller. Note that the first to fifth guide rollers 141 to 145 respectively rotate around shafts thereof.

The position detecting means 150 is provided between the fifth guide roller 145 and the sandwich belt conveyor 500. The position detecting means 150 detects a position where the side edge portion 11a of the first half region 11 and the side edge portion 12a of the second half region 12 are conveyed.

The position detecting means 150 is formed of a first sensor 151 which detects a position where the side edge portion 11a of the first half region 11 is conveyed and a second sensor 152 which detects a position where the side edge portion 12a of the second half region 12 is conveyed. The first sensor 151 and the second sensor 152 supply to the position control means 160 positional data showing detected positions where the both side edge portions 11a and 12a are being conveyed.

The position control means 160 is provided between the fifth guide roller 145 and the sandwich belt conveyor 500. The position control means 160 aligns the web 10 in the width direction (CD). The position control means 160 is formed of an oscillating roller 170 and an actuator 180.

The oscillating roller 170 changes the position of the web 10 in the width direction (CD). Specifically, the oscillating roller 170 rotates in response to the actuator 180 to be described later so as to change the positions where the side edge portion 11a of the first half region 11 and the side edge portion 12a of the second half region 12 are conveyed.

The oscillating roller 170 is formed of a first oscillating roller 171 and a second oscillating roller 172. The first oscillating roller 171 changes the position where the side edge portion 11a of the first half region 11 is conveyed by coming into contact with the first half region 11, and the second oscillating roller 172 changes the position where the side edge portion 12a of the second half region 12 is conveyed by coming into contact with the second half region 12.

The actuator 180 rotates the oscillating roller 170. The actuator 180 is formed of a first actuator 181 which rotates the first oscillating roller 171 and a second actuator 182 which rotates the second oscillating roller 172.

The first actuator 181 has data (first scheduled data) previously inputted therein which shows a schedule of the side edge portion 11a of the first half region 11 that is to pass the first sensor 151. The first actuator 181 compares the positional data supplied from the first sensor 151 and the first scheduled data, and rotates the first oscillating roller 171 in order to match the both side edge portions 11a and 12a of the web 10 which is folded in two.

Similarly, the second actuator 182 has data (second scheduled data) previously inputted therein which shows a schedule of the side edge portion 12a of the second half region 12 that is to pass the second sensor 152. The second actuator 182 compares the positional data supplied from the second sensor 152 and the second scheduled data, and rotates the second oscillating roller 172 in order to match the both side edge portions 11a and 12a of the web 10 which is folded in two.

The web 10 which passes the folding device 100 to be folded in two is conveyed to the sandwich belt conveyor 500. The sandwich belt conveyor 500 at least includes a first sandwich belt 501 winding around the multiple rollers R10, a second sandwich belt winding around multiple rollers R20, and driving means (unillustrated) which causes the first sandwich belt 501 and the second sandwich belt 502 to respectively wind around the multiple rollers R10 and around the multiple rollers R20. The two-folded web 10 is sandwiched by the first sandwich belt 501 and the second sandwich belt 502.

In general, a non-continuum of the absorbent article 1 or the like is divided in the conveyance direction, and thus is conveyed by a belt. On the other hand, a continuum of the web 10 or the like before being cut in the cutting process is not conveyed by a belt.

For example, when a continuum is conveyed by a belt, the continuum may sag or be pulled in the conveyance direction unless a conveyance speed of the continuum matches a driving speed of the belt. Moreover, installation of a belt conveyor is required, which results in an increase of a cost. For this reason, the use of the belt for conveying a continuum causes unnecessary worry.

Meanwhile, the web 10 (the first half region 11 and the second half region 12) is formed of a soft material. That is, the waistline regions 1A and 1B have a stretching property in the MD and the crotch region 1C has a stretching property in the CD. Note that the crotch region 1C has higher rigidity than that of the waistline regions 1A and 1B as being provided with the waterproof sheet 40 and the absorber 50.

Conventionally, it has been said that the web 10 having a stretching property is difficult to be conveyed. In particular, it is said that the second half region 12 is difficult to fold to the first half region 11 in the folding process. As described in the background of the invention, the first half region having a stretching property is conveyed with being partially supported by the multiple rollers provided at predetermined spacing, and is suspended in the air in portions between the multiple rollers.

At this time, the crotch region 1C of the web 10 on which the waterproof sheet 40 and the absorber 50 are laminated comes in contact with the guide means 140 or the folding center bar 130. As a result, the crotch region 1C gets behind the waistline regions 1A and 1B. Accordingly, there is a case where the second half region 12 is folded towards the first half region 11 with the crotch region 1C being twisted. This results in disfigurement of the absorbent article or generation of a manufacturing failure of the absorbent article in a process after the folding process.

Furthermore, if the second half region 12 is folded towards the first half region 11 with the crotch region 1C being twisted, the twist affects portions from the waistline regions 1A and 1B to the crotch region 1C. Accordingly, a distortion and a deformation entirely spread over the absorbent article. In particular, the twist affects greatly on the absorbent article having a stretching property.

In addition, in the conventional art, the web is suspended in the air between the multiple rollers. For this reason, the first half region 11 easily sags and thus is not conveyed stably. In particular, it is also difficult to match the side edge portion 12a of the second half region 12 and the side edge portion 11a of the first half region 11, since the second half region 12 is being folded while the first half region 11 is conveyed with being suspended in the air.

In contrast, in the present embodiment, in the folding process, the first half region 11 is conveyed on the conveyance belt 122 and the second half region 12 is folded towards the first half region 11 by the guide means 140 that guides the second half region 12.

According to this, the first half region 11 including the crotch region 1C having higher rigidity than those of the waistline regions 1A and 1B is conveyed on the conveyance belt 122. Therefore, even when the crotch region 1C of the web 10 on which the waterproof sheet 40 and the absorber 50 are laminated comes in contact with the folding center bar 130 or the guide means 140, the present embodiment can prevent that the conveyance of the second half region 12 gets behind the conveyance of the first half region 11.

Accordingly, the present embodiment can reduce the case that the second half region 12 is folded towards the first half region 11 with the crotch region 1C being twisted. Moreover, significant disfigurement of the absorbent article 1 or a manufacturing failure of the absorbent article 1 in the folding process can be prevented.

In addition, the second half region 12 is folded based on the first half region 11 conveyed on the conveyance belt 122. At this time, the first half region 11 is continuously conveyed in a planar state. Thus, the first half region 11 is not suspended in the air and does not sag on the conveyance belt 122. For this reason, the first half region 11 can be stably conveyed on the conveyance belt 122 and the side edge portion 12a of the second half region 12 easily matches the side edge portion 11a of the first half region 11 (that is, folding accuracy is improved).

In particular, the first half region 11 is conveyed in a state of being sucked on the conveyance belt 122. Accordingly, the first half region 11 is easily held substantially horizontally on the conveyance belt 122, and therefore the first half region 11 can be more stably conveyed. Moreover, the driving speed $v_1$ of the conveyance belt 122 is the same as the conveyance speed $v_2$ of the web 10, so that the first half region 11 can be prevented from sagging or being pulled in the conveyance direction.

Furthermore, the folding center bar 130 is positioned on the conveyance belt 122, so that the first half region 11 is sucked to a vicinity of the center line CL located between the first half region 11 and the second half region 12 on the conveyance belt 122. Accordingly, misalignment of the first half region 11 and the second half region 12 in the MD can be further prevented and the side edge portion 12a of the second half region 12 can more easily match the side edge portion 11a of the first half region 11.

In the present embodiment, in the folding process, the oscillating roller 170 is rotated by the actuator 180 to align the web 10 in the width direction. Accordingly, even in a case where the side edge portion 11a of the first half region 11 and the side edge portion 12a of the second half region 12 are almost misaligned with each other, the side edge portion 12a of the second half region 12 can match the side edge portion 11a of the first half region 11.

In the present embodiment, the web 10 being conveyed between the processes performed after the folding process (for example, between the folding process and the connecting process and between the connecting process and the cutting process) is conveyed with being held between the pair of the sandwich belts (the first sandwich belt 501 and the second sandwich belt 502). Accordingly, the web 10 can be conveyed with the side edge portion 11a of the first half region 11 and the side edge portion 12a of the second half region 12 matching each other. Thus, a manufacturing failure of the absorbent article 1 can be further suppressed.

(3) Other Embodiments

As described above, the content of the present invention has been disclosed by using the embodiment of the present invention. However, it should not be understood that the description and drawings which constitute one part of this disclosure limit the present invention.

Specifically, the conveyance rollers are described to be the first to fifth conveyance rollers R1 to R5 and the guide rollers are described to be the first to fifth guide rollers 141 to 145. However, the configuration is not limited to this. The number of the conveyance rollers and the guide means 140 may be, as a matter of course, any number.

The conveyance belt conveyor 120 is described to convey the first half region 11 horizontally in parallel to the supporting surface 101 of the folding device 100. However, the configuration is not limited to this. For example, the first half region 11 may be conveyed in an inclined state in relation to the supporting surface 101 of the folding device 100. In this case, the conveyance belt 122 is driven in an inclined state in relation to the supporting surface 101 of the folding device 100.

The conveyance belt conveyor 120 is described to include the suction means 123. However, the configuration is not limited to this, and any means may be employed other than the suction means 123 as long as the means can attach the web 10 onto the conveyance belt 122.

The actuator 180 is described to rotate the oscillating roller 170 so that the oscillating roller 170 aligns the web 10 in the width direction (CD). However, the configuration is not limited to this, and the actuator 180 may directly aligns the web 10 in the width direction (CD).

From this disclosure, various alternative embodiments, examples, and operational techniques will be apparent for a person skilled in the art. Accordingly, the technical scope of the present invention is defined only by the particular matters contained in the scope of claims which is appropriate from this disclosure.

What is claimed is:

1. A method of manufacturing an absorbent article, comprising the steps of:

forming a leg circumferential region on a web which is continuously fed in a conveyance direction on a conveyance belt; and folding the web along a center line, the folding bisecting a dimension of the web in a cross direction perpendicular to the conveyance direction to define first and second half regions respectively on two sides of the center line, so that the second half region comes closer to or overlaps the first half region, wherein said folding includes conveying the first half region on the conveyance belt while guiding the second half region towards the first half region by a guide unit including a plurality of guide rollers so that an inclination angle of the second half region in relation to the first half region becomes gradually smaller from the guide rollers on an upstream side to the guide rollers on a downstream side in the conveyance direction, in the folding, the first half region is conveyed by and sucked on the conveyance belt while the second half region, which is not sucked on the conveyance belt, is guided by said guide rollers towards the first half region so that a side edge of the second half region is flush with a side edge of the first half region in the conveyance direction, and during said folding, the second half region is guided by a pair of the guide rollers that directly sandwich the second half region therebetween.

2. The method according to claim 1, wherein in the folding, aligning the web in the cross direction by an actuator.

3. The method according to claim 1, further comprising,
after said folding, connecting the first half region and the second half region at a boundary region between two adjacent absorbent articles to be formed on the web, and
after the connecting, cutting the boundary region in the cross direction,
wherein after the folding, the web is conveyed while being held between a pair of conveyance belts.

4. The method according to claim 3, further comprising providing a folding center bar on the web between the first half region and the second half region during the folding and the connecting.

5. The method according to claim 1, wherein
the absorbent article is a disposable diaper with waistline members opposite to each other in the cross direction,
the web includes waistline regions corresponding to the waistline members and a crotch region positioned between the waistline regions,
the leg circumference region is provided on both sides of the crotch region in the conveyance direction,
each of the waistline regions has a stretching property in the conveyance direction, and
the crotch region has a stretching property in the cross direction.

6. The method according to claim 1, further comprising detecting a position of the web where both the side edge of the first half region and the side edge of the second half region are conveyed on the conveyance belt.

7. The method according to claim 6, further comprising adjusting the position of the web where the side edge of the first half region and the side edge of the second half region are conveyed after said folding the second half region onto the first half region.

8. The method according to claim 1, wherein said second half region of the web is not sucked on the conveyance belt until the side edge portion of the first half region and the side edge portion of the second half region contact with each other.

9. The method according to claim 1, wherein
before the folding, the web is fed in the conveyance direction by a plurality of first rollers, and
in the folding, the first half region of the web is conveyed on the conveyance belt in the conveyance direction while being pressed down by a second roller which has a larger diameter than said first rollers, the second roller having a dimension in the cross direction exceeding a half of the dimension of the web in the cross direction.

10. The method according to claim 1, wherein a driving speed of the conveyance belt is the same as a conveyance speed of the web.

\* \* \* \* \*